(12) United States Patent
Siddalingappa (10) Patent No.: US 10,716,774 B1
(45) Date of Patent: Jul. 21, 2020

(54) PHARMACEUTICAL COMPOSITIONS CONTAINING ISOTRETINOIN WITH IMPROVED DISSOLUTION PROFILE AND ENHANCED STABILITY

(71) Applicant: Yale Pharmaceuticals LLC, Princeton, NJ (US)

(72) Inventor: Basavaraj Siddalingappa, Gujarat (IN)

(73) Assignee: YALE PHARMACEUTICALS LLC, Princeton, NJ (US)

( * ) Notice: Subject to any disclaimer, the term of this patent is extended or adjusted under 35 U.S.C. 154(b) by 0 days.

(21) Appl. No.: 16/238,896

(22) Filed: Jan. 3, 2019

Related U.S. Application Data

(60) Provisional application No. 62/613,921, filed on Jan. 5, 2018.

(51) Int. Cl.
| | | |
|---|---|---|
| *A61K 31/203* | (2006.01) | |
| *A61K 9/14* | (2006.01) | |
| *A61K 47/24* | (2006.01) | |
| *A61K 9/00* | (2006.01) | |

(52) U.S. Cl.
CPC .......... *A61K 31/203* (2013.01); *A61K 9/0053* (2013.01); *A61K 9/146* (2013.01); *A61K 47/24* (2013.01)

(58) Field of Classification Search
CPC .................................................. A61K 31/203
See application file for complete search history.

(56) References Cited

U.S. PATENT DOCUMENTS

| | | | |
|---|---|---|---|
| 5,993,858 A | 11/1999 | Crison et al. | |
| 6,592,903 B2 | 7/2003 | Ryde et al. | |
| 6,605,298 B1 * | 8/2003 | Leigh ................... | A61K 9/0014 264/4.1 |
| 6,759,058 B1 | 7/2004 | Betageri | |
| 6,849,269 B2 | 2/2005 | Betageri | |
| 7,101,576 B2 | 9/2006 | Hovey et al. | |
| 7,259,186 B2 | 8/2007 | Cink et al. | |
| 7,435,427 B2 | 10/2008 | Vanderbist et al. | |
| 8,367,102 B2 | 2/2013 | Vanderbist et al. | |
| 8,952,064 B2 | 2/2015 | Vanderbist et al. | |
| 8,999,384 B2 | 4/2015 | Shafee et al. | |
| 9,078,925 B2 | 7/2015 | DeBoeck et al. | |
| 9,089,534 B2 | 7/2015 | Vanderbist et al. | |
| 9,445,995 B2 | 9/2016 | Betageri et al. | |
| 9,700,535 B2 | 7/2017 | Rao et al. | |
| 9,750,711 B2 | 9/2017 | Madan et al. | |
| 2007/0104780 A1 | 5/2007 | Lipari et al. | |
| 2014/0107203 A1 | 4/2014 | DeBoeck et al. | |
| 2016/0089353 A1 | 3/2016 | Rao et al. | |

FOREIGN PATENT DOCUMENTS

| | | |
|---|---|---|
| EP | 0149197 A2 | 7/1985 |
| EP | 1158959 B1 | 12/2011 |
| WO | 2004084883 A1 | 10/2004 |
| WO | 2013168167 A1 | 11/2013 |
| WO | 2015186039 A1 | 12/2015 |
| WO | 2016051288 A1 | 4/2016 |
| WO | 2016189481 A1 | 12/2016 |
| WO | 2016193779 A1 | 12/2016 |

OTHER PUBLICATIONS

Basavaraj, Siddalingappa, et al., "Improved oral delivery of resveratrol using proliposomal formulation: investigation of various factors contributing to prolonged absorption of unmetabolized resveratrol." Expert opinion on drug delivery 11, No. 4 (2014), pp. 493-503.
Chavda, Hitesh, et al., "Self-nanoemulsifying powder of isotretinoin: preparation and characterization." Journal of Powder Technology vol. 2013, Article ID 108569, 9 pages, (2013).
Patel, M. R., et al., "Improving the isotretinoin photostability by incorporating in microemulsion matrix", ISRN pharmaceutics, vol. 2011, Article ID 838016, 6 pages.

* cited by examiner

*Primary Examiner* — Samira J Jean-Louis
(74) *Attorney, Agent, or Firm* — Lucas & Mercanti, LLP (57) ABSTRACT

Isotretinoin compositions having improved bioavailability are disclosed. The compositions are oral formulations containing isotretinoin, a lipid excipient and a cosolvent, wherein the ratio of isotretinoin to the lipid excipient is from about 1:1.2 to about 1:1.6. The compositions can be in the form of a pharmaceutically acceptable oral dosage form such as a capsule or compressed tablet wherein the isotretinoin is adsorbed onto blended particles of a cellulosic polymer and silicon dioxide in combination with a lipid excipient such as soy phosphatidylcholine and a cosolvent such as propylene glycol. Methods of preparing the compositions and methods of treatment using the compositions are also disclosed.

17 Claims, 5 Drawing Sheets

Figure 1: Dissolution profile of Isotretinoin capsule formulations Form 4-11 as compared to a Control, in water containing 2.5% SLS, 1000 mL.

Figure 2: Plasma-time profile of Isotretinoin formulations after oral dosing to Male Sprague Dawley rats (Fasting) after oral dosing (Form 3-11).

Figure 3: Pharmacokinetic profile of Form 12 and Absorica in Male Wistar Rats.

Figure 4

Figure 5: Human Bioequivalence data for Form 13A vs 13B

PHARMACEUTICAL COMPOSITIONS CONTAINING ISOTRETINOIN WITH IMPROVED DISSOLUTION PROFILE AND ENHANCED STABILITY

CROSS-REFERENCE TO RELATED APPLICATIONS

This application claims the benefit of priority from U.S. Provisional Patent Application Ser. No. 62/613,921 filed Jan. 5, 2018, the contents of which are incorporated herein by reference.

FIELD OF INVENTION

Present invention relates to pharmaceutical compositions containing isotretinoin, a cosolvent and lipid excipient.

BACKGROUND OF THE INVENTION

Poorly soluble drugs are often associated with low and variable bioavailability. To achieve the desired therapeutic levels in the blood, poorly soluble drugs need to be administered at higher dose and some drugs need to be administered with food.

Isotretinoin is an orally active retinoic acid derivative for the treatment of severe refractory nodulocystic acne. Peak plasma concentrations of Isotretinoin were reported to vary widely among individuals, but usually occur 2 to 4 hours after administration. Steady-state concentrations were also subject to considerable inter-individual variation. After multiple dosing, the major systemic metabolite of isotretinoin in man is 4-oxo-isotretinoin, and its plasma concentration is about 4-fold higher than that of the parent drug. The elimination half-life of isotretinoin has been reported as about 10 to 20 hours in several studies in healthy subjects or patients (Ward A et. al Drugs. 1984; 28(1):6-37).

Solubility and permeability are two important parameters that determine the rate and extent to which the drug molecules reach systemic circulation. Drug levels in the blood within a therapeutic window are necessary to achieve the therapeutic benefit of the molecule. Poor and variable bioavailability may lead to a poor therapeutic outcome and reduced patient compliance. Repeated dosing and meal restrictions also contribute to increased patient complaints.

Apart from solubility, poor permeability, extensive first pass metabolism and drug efflux mechanism also contribute to poor bioavailability. Formulating poorly soluble drugs in a lipid-based composition may also improve permeability and reduce metabolism and efflux presumably via alternative lymphatic uptake. The present invention addresses this need.

SUMMARY OF THE INVENTION

In accordance with a first aspect of the invention there are provided oral formulations comprising isotretinoin, a lipid excipient and a cosolvent, wherein the ratio of isotretinoin to the lipid excipient is from about 1:1.2 to about 1:1.6. In some preferred embodiments, the ratio is from about 1:1.3 to about 1:1.5. In a further aspect of the invention, the oral compositions are powder compositions containing isotretinoin, a lipid excipient, a cosolvent, a cellulosic polymer, silicon dioxide and optionally, an antioxidant. The cellulosic polymer and the silicon dioxide are present as a binary mixture of particles and the isotretinoin, the lipid excipient, the cosolvent, and the antioxidant are adsorbed on the particles of the binary mixture. The lipid excipient is preferably a phospholipid such as soy phosphatidylcholine—also known as soya PC—and the cosolvent is preferably propylene glycol or polyethylene glycol with Mw<600 (hereinafter PEG).

In an alternative embodiment, powder compositions include one or more inert pharmaceutical excipients which have high solvent adsorption capacity, as described in more detail below optionally in a binary mixture with silicon dioxide, and the isotretinoin, a lipid excipient, one or more cosolvents, and optional antioxidant are adsorbed on the particles of one or more inert pharmaceutical excipients which have high solvent adsorption capacity, and, if present, silicon dioxide.

Further aspects of the invention include methods of preparing the compositions as well as methods of treating isotretinoin-responsive conditions using the compositions described herein.

DETAILED DESCRIPTION OF THE INVENTION

Pharmaceutical compositions of this invention include oral lipid formulations of isotretinoin with improved dissolution, bioavailability and stability. The compositions include at least one cosolvent and one lipid excipient, and, in many embodiments, one or more inert pharmaceutical excipients which have high solvent adsorption capacity. It has been surprisingly found that therapeutically advantageous oral formulations can be provided when the ratio of the isotretinoin to lipid excipient is maintained within specific ranges. Such oral formulations comprise isotretinoin, a lipid excipient and a cosolvent, wherein the ratio of isotretinoin to the lipid excipient is from about 1:1.2 to about 1:1.6. In some preferred embodiments, the ratio is from about 1:1.3 to about 1:1.5.

In accordance with the foregoing, there are provided in one embodiment powder compositions comprising isotretinoin, a lipid excipient, a cosolvent, a cellulosic polymer, silicon dioxide and optionally, an antioxidant. The cellulosic polymer and the silicon dioxide or, in an alternative embodiment, the pharmaceutical excipients having high solvent adsorption capacity optionally combined with silicon dioxide, are present as a blend or a substantially uniform mixture of particles. In most aspects, the particles will be present as a binary mixture of particles. The isotretinoin, the lipid excipient, the cosolvent(s), and, if included, the antioxidant are adsorbed on the binary mixture, e.g. the cellulosic polymer and the silicon dioxide particles or the pharmaceutical excipients having high solvent adsorption capacity optionally in combination with silicon dioxide.

For purposes of the present invention, it will be understood that the cellulosic polymer and silicon dioxide are in particle form and that as such, are easily formed into a blend. The blend can be, but is not necessarily, a homogeneous blend of the particles. In most embodiments, it is envisioned that the cellulosic polymer particles and silicon dioxide particles will be dry blended using a pharmaceutically acceptable blending apparatus.

It will also be appreciated that the components used to make the compositions of the invention will be pharmaceutically acceptable as such term is understood by those of ordinary skill.

Isotretinoin, also known as 13-cis-retinoic acid, is well known to those of ordinary skill and can be obtained from commercial sources. Also contemplated for inclusion herein is isotretinoin in the form of a salt, or an ester. The amount of isotretinoin in the powder compositions can vary according to the desires of the artisan, however it is contemplated that most compositions in accordance with the invention will contain from about 2 to about 20% wt. isotretinoin, with amounts of from about 5 to about 15% wt. being preferred in alternative embodiments. In some aspects of the invention the particle size of the isotretinoin is about D90<150 μm or about D90<125 μm or about D90<100 μm.

The powder compositions of the invention include a lipid excipient which is preferably a phospholipid. A non-limiting list of suitable phospholipids includes distearoyl phosphatidylcholine, dipalmitoyl phosphatidylcholine, dimyristoyl phosphatidylcholine, egg phosphatidylcholine, soy or soya phosphatidylcholine, dimyrsityl phosphatidyl glycerol sodium, 1,2-dimyristoyl-phosphatidic acid, dipalmitoyl-phosphatidylglycerol, dipalmitoyl phosphate, 1,2-distearoyl-sn-glycero-3-phospho-rac-glycerol, 1,2-distearoyl-sn-glycero-3-phosphatidic acid, phosphatidylserine and sphingomyelin. Such materials are available from commercial sources. In some preferred embodiments, the phospholipid is soy phosphatidylcholine. The purified phosphatidylcholine is obtained from soya beans, which contains not less than 94% of phosphatidylcholine by HPLC. The product does not contain more than 4% of lysophophatidyl choline. The peroxide levels maintained <3.0 and non-polar lipids present below 3%. The pure phosphatidyl choline from soya beans is soluble in ethanol, propylene glycol, PEG 400 and other organic solvents. Purified lecithin or phosphatidyl choline from soya are available commercially Phospholipon 90 G or H (Lipoid), L-α-Lecithin, Soybean (Merck-Millipore and Calbiochem), Soy PC 95%, Egg PC 95%, Hydro Soy PC, Hydro Egg PC (Avanti Polar Lipids, Inc, USA). The amount of the lipid excipient included in the powder compositions can range from about 5 to about 30% wt., with amounts ranging from about 5 to about 15% wt. being preferred in alternative embodiments. Mixtures of the foregoing are also contemplated. For purposes of the present invention, soy and soya are understood to be interchangeable.

In another aspect of the invention, the particle component of the powder compositions can include one or more inert pharmaceutical excipients which have high solvent adsorption capacity. This means, if water or any organic solvents, if mixed with such excipients at certain portions, the excipients will adsorb such solvents, become dense and still remain free flowing. A non-limiting list of suitable excipients include cellulosic polymers, starches, silicon dioxide, sugars such as lactose or sugar-based polymers, mesoporous silica, inorganic salts, such as calcium phosphate or dicalcium phosphate. Wherever preferable, mixture of such excipients can be employed to achieve larger benefits of solvent adsorption, stability and dissolution. For example, higher molecular weight PEG's, i.e. 2,000-100,000, preferably 6,000-8,000, can be included as an auxiliary or supplemental cosolvent or solubilizer to improve wettability of the drug/lipid mixture in aqueous media.

The cellulosic polymers useful in compositions of the present invention include pharmaceutically acceptable microcrystalline celluloses such as those having the properties of high surface area, low bulk density and higher solvent adsorption capacity. Such grades of MCC are commercially available from Asahi Kasei as Ceolus KG 1000. Alternatives include microcrystalline cellulose USP-NF, Avicel, etc., all of which will be readily apparent to those of ordinary skill.

Some preferred $SiO_2$ include those which are characterized as hydrophilic fumed silica products which are pharmaceutical grade and have a BET surface area of from about 90 to about 300 $m^2/g$ with preferably those having a BET surface area of about 200 $m^2/g$. Such products are well known to those of ordinary skill and available from commercial sources such as Evonik under the tradename of Aerosil 200, Aerosil 300, etc. Mixtures of the foregoing are also contemplated. The mixture of cellulosic polymer and silicon dioxide is the preferred excipient. The selected cellulosic polymer and silicon dioxide preferably have solvent adsorption capacity between 10-60% W/W.

The cosolvents included in the compositions of the present invention include solvents such as aliphatic alcohols, e.g. ethanol being preferred, polyethylene glycols, preferably those having a molecular weight of from 200 to about 600 with MW's of about 400 being preferred, propylene glycol, dimethyl formamide, dimethyl acetamide, and glycerin. Mixtures of the foregoing are also contemplated. In some preferred embodiments, the cosolvent is propylene glycol or PEG or mixtures of propylene glycol and low MW PEGs thereof. The amount of cosolvent(s) included in the compositions of the present invention can be from about 5 to about 30% wt., with amounts of from about 6 to about 15% wt. being preferred in alternative embodiments.

The pharmaceutical compositions of the present invention also include an amount of an antioxidant. Such amounts can be in the range of from about 0.1 to about 10% wt., with amount of from 0.2 to about 5% being preferred in alternative embodiments. A non-limiting list of suitable anti-oxidants includes, without limitation, for example BHA (butylated hydroxyl anisole), EDTA (ethylenediaminetetraacetic acid), BHT (butylated hydroxy toluene), propyl gallate, ascorbyl palmitate (L Ascorbic acid 6-palmitate) and mixtures thereof.

In further aspects of the invention, the powder compositions can include one or more pharmaceutically acceptable diluents, adsorbents, binders, lubricants, disintegrants, glidants, colorants, sweeteners, flavors, viscosity building agents, pH modifiers in amounts which can be determined by those of ordinary skill without undue experimentation.

In some embodiments, the composition of inventions can be in semisolid forms, wherein the dispersion containing Isotretinoin, Soya PC, and cosolvent can be filled into softgel capsules.

While the compositions of the invention can be in the form of a dry powder, it will be understood that the moisture content of the compositions is not necessarily zero %. It is contemplated that the powder compositions will have a moisture content of 0.5 to about 10% in many aspects and less than about 3% in other aspects. The powder compositions are free-flowing and can easily be incorporated into pharmaceutically acceptable oral dosage forms such as capsules or compressed tablets using a capsule filling machine or tablet press well known to those of ordinary skill. It is contemplated that the amount of pharmaceutical dosage forms will contain a therapeutically acceptable amount of isotretinoin. This amount is generally within the range of from about 1 to about 50 mg per dosage form. Amounts of from about 5 to about 40 mg are also contemplated as well as dosage forms containing 5 mg, 10 mg, 20 mg, 25 mg, 30 mg, 35 mg or 40 mg.

In another embodiment of the invention there are provided methods of preparing the powder-based isotretinoin containing compositions described herein. The methods include:

a) providing a liquid mixture comprising a lipid excipient and a cosolvent;

b) combining the liquid mixture of step a) with an antioxidant, if desired, to form a dispersion containing the lipid excipient, cosolvent and antioxidant;

c) combining the dispersion resulting from step b) or if no antioxidant is included, the liquid mixture of step a) with isotretinoin under conditions to maintain a dispersion; and d) combining the dispersion resulting from step c) with optional additional cosolvent/solubilizer; and e) mixing the dispersion of step c) or, if used, the dispersion of step d) with a blend of cellulosic polymer particles and silicon dioxide particles under conditions sufficient to cause the isotretinoin, antioxidant, lipid excipient, and cosolvent to be adsorbed on the cellulosic polymer particles and silicon dioxide particles in the blend to form a powder-based isotretinoin composition. The resulting compositions can be transformed into pharmaceutically acceptable dosage forms such as compressed tablets or capsules using techniques readily apparent to those of ordinary skill.

The amounts of each ingredient are the same as that set forth above with respect to the powder compositions. The cellulosic polymer and silicon dioxide are both in particle form and are combined as a simple binary mixture using dry blending techniques before being contacted with the liquid dispersion components. The final powder composition results from the combining of the dispersion ingredients with the dry blend of cellulosic polymer and silicon dioxide and triturating the ingredients until all of the liquid dispersion is completely adsorbed onto the mixture of particles of cellulosic polymer and silicone dioxide. For purposes of the present invention, trituration shall be understood to mean the production of a homogeneous material by mixing the component materials thoroughly. It is also to be understood and appreciated that as a result of the trituration of the dispersion and particle blend that it is not necessary for every particle of the blend to include each ingredient of the dispersion. However, the composition, which is in the form of a powder will include a plurality of particles of both cellulosic polymer and silicon dioxide having all of the dispersion components adsorbed thereon. The trituration process can simply be achieved at industrial scale using appropriate machines, high shear mixer, planetary mixer and mass mixer are the few machines to mention.

The powder compositions of the present invention have advantageous physical properties compared to isotretinoin compositions of the prior art. As will be seen in the examples below, the compositions demonstrate high levels of isotretinoin dissolution in aqueous environments. For example, the compositions demonstrate amounts of isotretinoin dissolved after 4 hours in an aqueous solution of at least about 75%, with amounts of at least about 80% or at least about 90% being shown as well.

The powder compositions also demonstrate unexpectedly advantageous pharmacokinetic properties in vivo. For example, as shown below, the compositions provide an $AUC_{0-6}$ after a 6 mg/kg dose of isotretinoin of at least about 12 µg*hr/mL after oral dosing to fasting Wistar rats in some embodiments with an $AUC_{0-6}$ after a 12 mg/kg dose of isotretinoin of at least about 12 µg*hr/mL after oral dosing to fasting Wistar rats in other embodiments, an $AUC_{0-6}$ after a 12 mg/kg dose of isotretinoin of at least about 18 µg*hr/mL after oral dosing to fasting Wistar rats in still further embodiments and an $AUC_{0-6}$ after a 12 mg/kg dose of isotretinoin of at least about 21 µg*hr/mL after oral dosing to fasting Wistar rats in yet further embodiments. Another desirable pharmacokinetic property for the compositions is that they provide a $C_{max}$ after 6 mg/kg dose of about 4.1 µg/mL after oral dosing to fasting Wistar rats.

The dosing suspensions were prepared by taking the content of one capsule of Absorica-40 mg or powder weight equivalent to 40 mg or 20 mg of Isotretinoin formulations of this invention in 5 mL water, the mixtures were sonicated with intermittent shaking till a uniform yellowish to orange colored dispersions were formed. The dispersions were further mixed with 5 mL solution of 0.5% W/V sodium carboxy methyl cellulose as suspending agent. The final concentration of dosing preparation was 4 mg/mL for Absorica, 4 mg/mL and 2 mg/mL for Test formulations.

Another advantageous property associated with the compositions of the invention is that they demonstrate improved stability. As can be seen from the examples below, the peak purity of the isotretinoin in the compositions after 5 days at 60° C. is at least about 98%, preferably at least about 98.5% and more preferably at least about 99%. As such, it is possible to provide orally acceptable pharmaceutical dosage forms in the form of a capsule having improved stability especially when the capsules are packed in an aluminum pouch or any other suitable moisture resistant package. Stability for the capsules has been shown to be at least 3 months at 40° C./75% RH with the total impurity in the product <5%.

The invention also includes methods of treating isotretinoin-responsive conditions in mammals such as humans. The methods include administering an effective amount of the isotretinoin-containing compositions described herein to a mammal in need thereof. It is contemplated that the amount effective for treatment of the conditions will be apparent to those of ordinary skill and clinical presentation. The isotretinoin-containing compositions are preferably in the form of a pharmaceutically acceptable oral dosage form such as a capsule or a compressed tablet containing a suitable amount of isotretinoin for daily administration or as frequently as desired by the clinician administering the drug. For example, the compositions of the invention can be prepared as oral dosage forms containing sufficient isotretinoin for effective treatment of an indicated condition, e.g. part of a once daily or twice daily oral therapy regimen. In this aspect of the invention, suitable oral dosage forms can contain, for example, from about 0.1 to about 50 mg of isotretinoin. Alternatively, the compositions can contain sufficient isotretinoin to provide administration of from about 0.05 to about 2 mg/kg per day in a single or in divided doses. In yet further embodiments, the amount of isotretinoin administered as part of the inventive compositions is sufficient to provide in single or divided doses one of the following:
- a. from about 0.5 to about 1 mg/kg/day;
- b. from about 0.2 to about 0.4 mg/kg/day;
- c. from about 0.25 to about 0.49 mg/kg/day;
- d. about 0.25 mg/kg/day; or
- e. about 0.35 mg/kg/day.

It many aspects of this embodiment, the total daily amounts of isotretinoin are administered in two divided doses, e.g. 0.5-1.0 mg/kg/day, with half of the desired amount given twice daily.

EXAMPLES

The following examples serve to provide further appreciation of the invention but are not meant in any way to restrict the effective scope of the invention.

Example 1: Isotretinoin Compositions with Adsorbent Excipients

In these examples, compositions with soya PC solutions were adsorbed onto excipients with greater adsorption capacity, such as MCC and Aerosil. Antioxidants were also included. Resulting compositions were evaluated for dissolution and selected formulations were also tested for absorption profile in rats. (Note: for dissolution, powder equivalent to 40 mg of Isotretinoin was used for dissolution in HPMC capsules size 00)

was triturated until all of liquid dispersion was completely adsorbed onto MCC-Aerosil mixture. (Same process was used for Form 3-Form 11).

Figure 1:
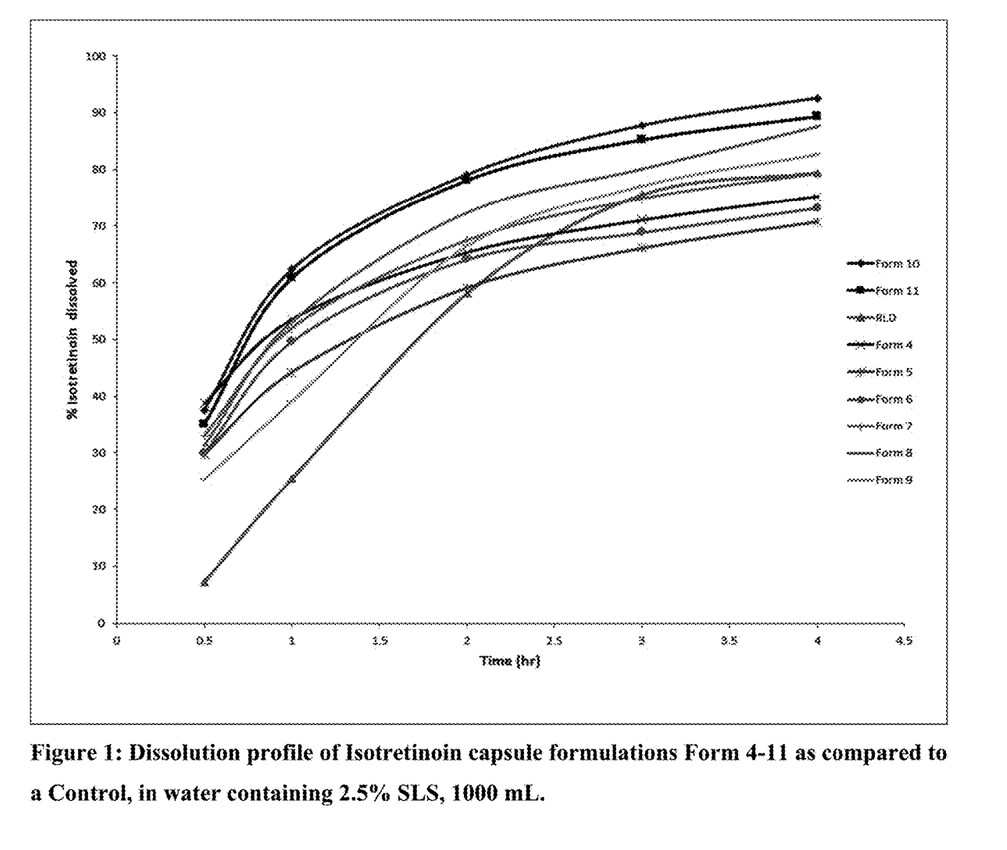
FIG. 1 is a graph showing the dissolution profile of isotretinoin capsule formulations designated Forms 4-11 prepared in accordance with Example 1 and as compared to a Control, in water containing 2.5% SLS, 1000 mL.

Turning now to FIG. 1, it can be seen that the dissolution profile of isotretinoin Formulations 4-11 indicates that the inclusion of inert adsorbent excipients such as MCC and Aerosil did not negatively affect the dissolution. Inclusion of such excipients however was used to convert the liquid dispersions into free flowing powder masses which can be filled in hard shell capsules. The MCC Ceolus KG-1000 and Aerosil-200 have greater liquid adsorption capacities. Hence the formulation made it feasible to be filled into hard capsules.

Another interesting observation from this set of examples is that the dissolution increases as a function of the amount of soya PC in the formulation. Unlike other reports (Basavaraj et al 2014, Nekkanti et al 2016, Yanamandra et al 2014, Betageri et al 2014 U.S. Pat. No. 9,445,995 B2) where rate and extent of dissolution do not increase as a function of phospholipids, here we saw a greater increase in both rate and extent of dissolution as amount of soya PC increases in the formulation.

Example 2 Pharmacokinetic Studies of Isotretinoin Formulations in Rats

Isotretinoin formulations were also tested for rat pharmacokinetic studies in male Sprague Dawely rats for first set of formulations. The dosing dispersions were prepared by taking formulation weight equivalent to 40 mg of Isotretinoin dispersed in 5.0 mL of water first and 5.0 mL of 0.5% w/v sodium carboxy methyl cellulose (Na CMC) was added to the dispersion as suspending agent. Final disper-

TABLE 1

Isotretinoin formulations with adsorbent excipients and antioxidants.

| Ingredients | Mg/Capsule | | | | | | | | |
| --- | --- | --- | --- | --- | --- | --- | --- | --- | --- |
| | F3 | F4 | F5 | F6 | F7 | F8 | F9 | F10 | F11 |
| Isotretinoin | 40.000 | 40.000 | 40.000 | 40.000 | 40.000 | 40.000 | 40.000 | 40.000 | 40.000 |
| Soya PC | 23.600 | 44.000 | 48.645 | 51.613 | 52.903 | 54.155 | 55.523 | 56.774 | 68.129 |
| Propylene glycol | 29.333 | 55.467 | 60.903 | 64.516 | 67.742 | 68.903 | 70.581 | 72.258 | 86.710 |
| PEG 8000 | 133.333 | 133.333 | 100.645 | 100.645 | 100.645 | 100.645 | 100.645 | 100.645 | 100.645 |
| MCC | 179.733 | 132.000 | 180.645 | 174.194 | 174.194 | 167.742 | 164.645 | 218.065 | 192.258 |
| Aerosil-200 | 8.000 | 8.000 | 59.355 | 59.355 | 59.355 | 59.355 | 59.355 | 7.742 | 7.742 |
| B HA | 0.000 | 0.000 | 0.968 | 0.968 | 0.968 | 0.968 | 0.968 | 0.968 | 0.968 |
| EDTA | 0.000 | 0.000 | 4.839 | 4.839 | 4.839 | 4.839 | 4.839 | 4.839 | 4.839 |
| BHT | 0.000 | 0.000 | 0.400 | 0.400 | 0.400 | 0.400 | 0.400 | 0.400 | 0.400 |
| Total | 414.000 | 412.800 | 496.400 | 496.529 | 501.045 | 497.006 | 496.955 | 501.690 | 501.690 |

Formulations 3-11 were prepared by a process that involves preparation of soya PC solution in propylene glycol, the isotretinoin was wetted with Soya PC solution by stirring the dispersion of isotretinoin in Soya PC solution for 5-15 minutes, antioxidants, and PEG were added to dispersion and stirred for about 5-15 minutes. To the dispersion containing the soya PC solution, Isotretinoin, antioxidants and PEG, premixed blend of MCC and Aerosil which was passed through 30/40 mesh sieve was added. The mixture sion had 4 mg/mL of Isotretinoin and 0.25% W/V of Sodium CMC. The rats were dosed at 12 mg/kg of Isotretinoin. The blood was collected at 0.5, 1, 2, 4 and 6 hr. The plasma was separated by centrifuging blood. The plasma was then mixed with appropriate amount of acetonitrile to precipitate protein. Plasma samples of Form 3, 4 and RLD-1 were analyzed by LC-MS (Used Megesterol acetate as internal standard). Since the levels observed were detectable in HPLC, the rest of the plasma samples were analyzed by HPLC. See FIG. 2.

TABLE 2

Pharmacokinetic parameters of Isotretinoin formulation (Fasting Rats)

| Parameter | RLD-1 | RLD-2 | Form 3 | Form 4 | Form 7 | Form 10 | Form 11 |
|---|---|---|---|---|---|---|---|
| Lipid/Drug ratio | Not applicable | Not applicable | 0.59 | 1.10 | 1.32 | 1.41 | 1.70 |
| % Dissolved (4 h) | 79.4% | 79.4% | Not done | 75.2% | 79.26% | 92.59% | 89.31% |
| AUC (ug · h/mL) | 9.093 | 12.96 | 4.89 | 6.92 | 12.74 | 21.61 | 18.45 |
| C max ug/mL | 1.76 | 1.53 | 1.09 | 1.20 | 1.75 | 3.23 | 3.02 |

Figure 2:
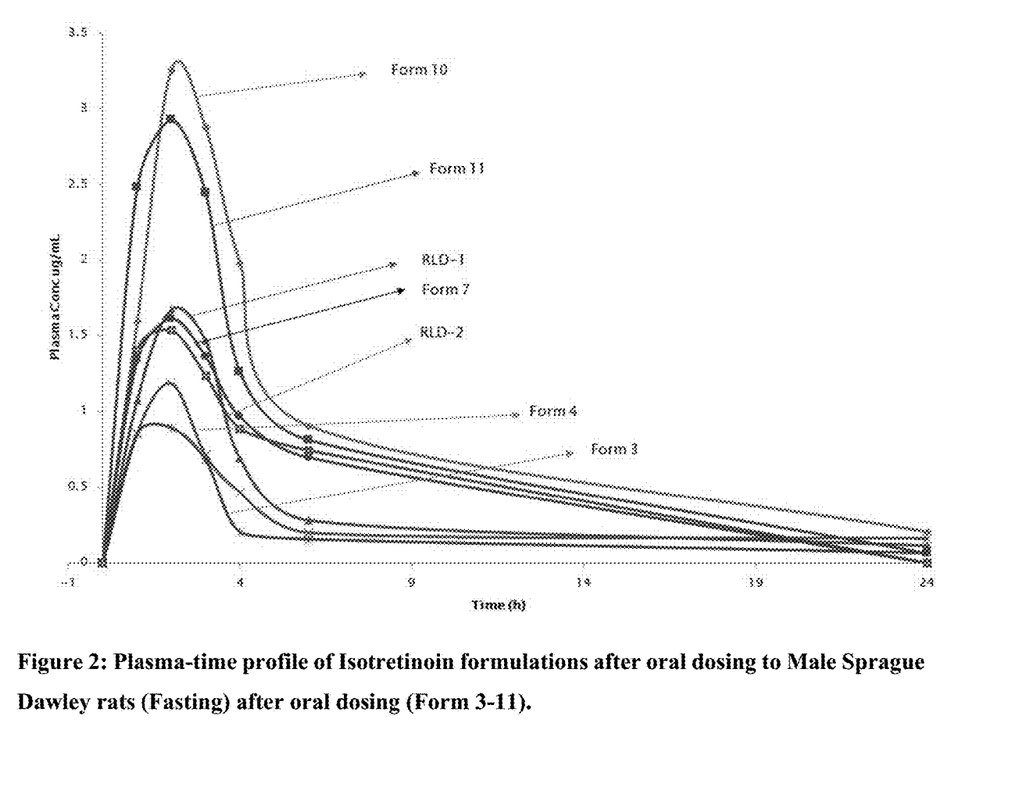
FIG. 2 is a graph showing a plasma-time profile for Isotretinoin formulations prepared in accordance with the present invention in Example 2 as Form 3-11, after oral dosing to Male Sprague Dawley rats (Fasting).

FIG. 2 and Table 2 data indicate that absorption of Isotretinoin increases as the concentration of soya PC in the formulation increases. The absorption of Isotretinoin of the present invention shows a trend that some of the formulations with higher soya PC concentration show greater absorption than the most bioavailable product, Epuris/Absorica, in the market. In fasting conditions, Absorica/Epuris are reported to have the highest bioavailability compared to other brands of Isotretinoin.

Example 3

In order to test for any unexpected outcome, increased absorption of Isotretinoin as a function of increased Soya PC levels in the capsules, the dose of Isotretinoin was reduced to half and compared against a double dose of Absorica (20 mg Test vs Absorica-40 mg).

The Form-12 was prepared in same manner as of Form-3-11, instead of BHA, BHT and EDTA, propyl gallate and ascorbyl palmitate were used as antioxidant. The process of incorporation of each ingredient remained the same.

Suspensions for Rat Pharmacokinetic were similar manner as in the previous example, Form-12, one capsule content equivalent, was dispersed in 10 mL dosing vehicle (2 mg/mL) and Absorica-40 mg, at 40 mg per 10 mL (4 mg/mL). Dosing volumes (mL/kg body weight of rats) were maintained the same for both formulations.

TABLE 3

Reduced dose Isotretinoin formulation for Rat PK studies.

| | Form 12 | |
|---|---|---|
| Ingredients | Mg/Capsule | % Wt/Wt |
| Isotretinoin | 20.00 | 5.02 |
| Soya PC | 52.87 | 13.26 |
| Propylene glycol | 52.87 | 13.26 |
| PEG 4000 | 20.00 | 5.02 |
| MCC (Ceolus Kg 1000) | 165.00 | 41.38 |
| Aerosil 200 | 80.00 | 20.06 |
| Ascorbyl palmitate | 6.00 | 1.50 |
| Propyl gallate | 2.00 | 0.50 |
| Total | 398.75 | 100.00 |

TABLE 4

Pharmacokinetic parameters of Form 12 and Absorica in Wistar Rats.

| Parameter | Absorica 12 mg/kg | Form 12 6 mg/kg |
|---|---|---|
| AUC 0-6 | 12.6 | 12.43 |
| Cmax | 4.40 | 4.10 |

Figure 3:
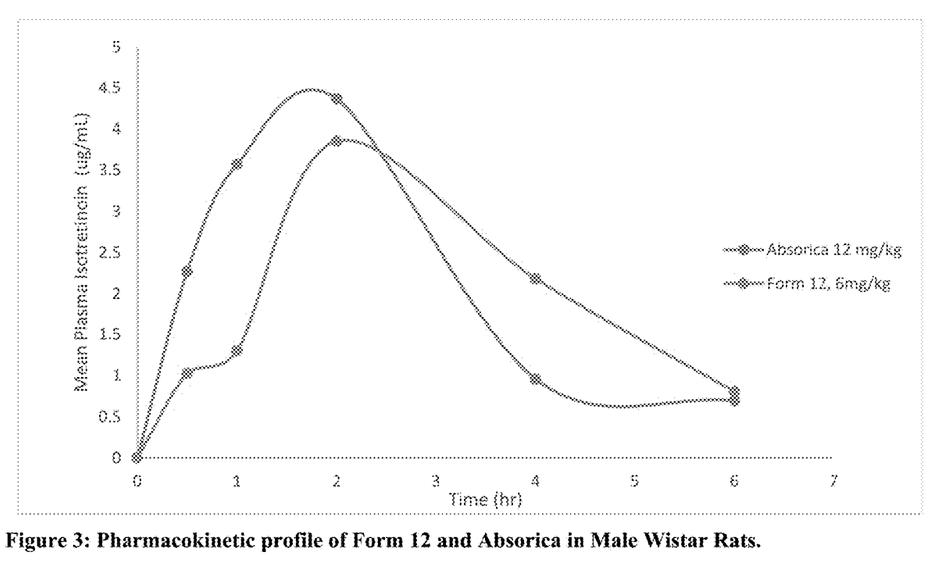
FIG. 3 is a graph showing the pharmacokinetic profile of reduced dose formulation prepared in accordance with Example 3 as Form 12 as compared to Absorica in Male Wistar Rats.

See also FIG. 3.

The Formulation 12 and Absorica were also tested for absorption profile in Male Wistar rats. Formulation 12 was dosed at 6 mg/kg, while Absorica was dosed at 12 mg/kg. The rest of the procedure was similar to the rat study with Sprague Dawley rats.

The pharmacokinetic profile of Isotretinoin formulations from Form 3 to Form 11 indicates an upward trend was observed with the Isotretinoin formulations, i.e. the absorption of Isotretinoin increased as a function of Soya PC concentration in the formulation. The absorption seemed to saturate at about Soya PC:Drug ratio of about 1.41. The AUC and $C_{max}$ of some of the formulations (Form 10 and 11) are close to double of the Epuris at the same dose. This indicates the positive effect of soya PC on in vivo dissolution of Isotretinoin in the GIT.

Figure 4:
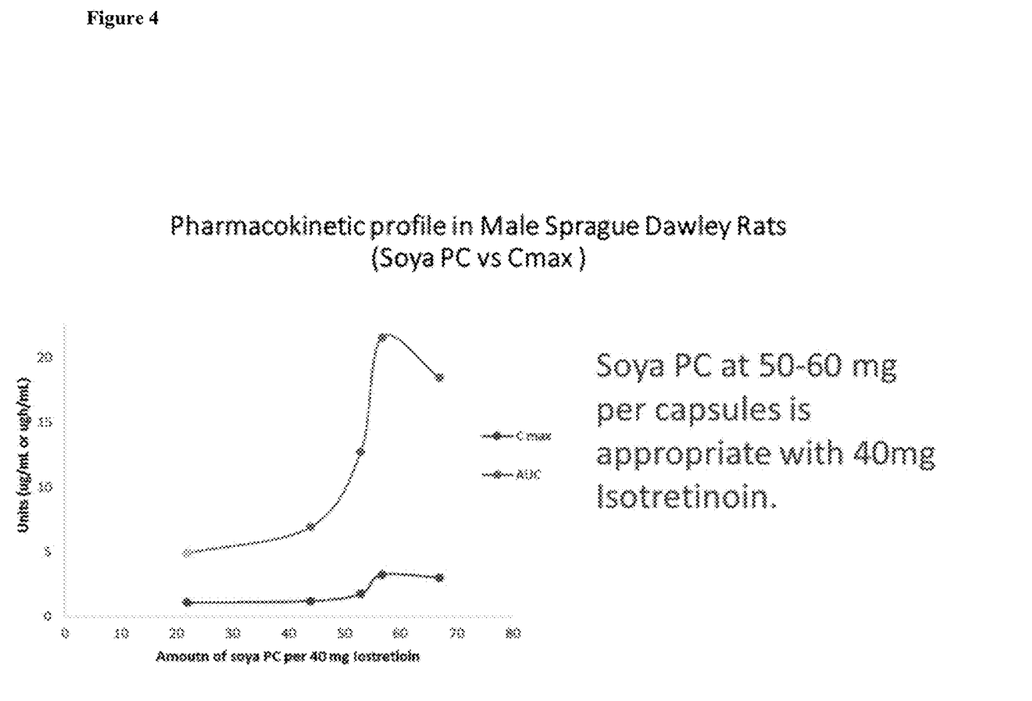
FIG. 4 is a graph showing pharmacokinetic profiles of isotretinoin formulations described in Example 3 depicting role of Soya PC in Male Sprague Dawley Rats.

Turning now to FIG. 4, it can be seen that increasing the amount of soya PC in the capsule and therefore with respect to the isotretinoin improved absorption of the drug in the rats, however, the effect is not linear. In fact, it was unexpectedly found that there was a synergistic benefit when the ratio of drug to soya PC rose above about 1:1.2 and diminishing effects were observed when the ratio of drug to soya PC exceeded about 1:1.6.

The Pharmacokinetic profile of Form 12 in comparison with Absorica, it is evident that AUC and $C_{max}$ of Form 12 at 6 mg/kg are equivalent to those of Absorica at 12 mg/kg. So, at half the dose, Form 12 is equivalent to a full dose of Absorica in terms of bioavailability. Hence, the dose of Isotretinoin can be reduced with formulations of this invention. This was an unexpected benefit of the formulations of the invention.

Example 4: Isotretinoin Formulations Compared to Absorica in Human Bioequivalence Study In this example, two formulations were made in accordance with the procedures of Example 1 according to the formulae below:

TABLE 5

| Ingredients | 13A Mg/Capsule | 13B Mg/Capsule |
| --- | --- | --- |
| Isotretinoin | 40.00 | 40.00 |
| Soya PC | 52.90 | 53.50 |
| Propylene glycol | 52.90 | 54.00 |
| PEG 8000 | 20.00 | 30.00 |
| MCC (Ceolus Kg 1000) | 170.20 | 164.50 |
| Aerosil 200 | 80.00 | 80.00 |
| Ascorbyl palmitate | 12.00 | 12.00 |
| Propyl gallate | 2.00 | 2.00 |
| Total | 436.00 | 436.00 |

The test products of Form-13A and B were tested for bioequivalence against Absorica-40 in male human volunteers. An Open Label, Balanced, Randomized, Two-Treatment, Two Period, Two-Sequence, Crossover, Single Oral Dose, Bioequivalence Study was carried out to ascertain the equivalence of Test-40 mg vs reference Absorica-40 mg in fasting conditions. The ratio of Test/Reference for AUC0-t, AUC0-inf and Cmax were calculated.

TABLE 6

Human Pharmacokinetic data for Form-13A and Absorica-40 mg

| Product | $AUC_{0-t}$ | $AUC_{0-inf}$ | $C_{max}$ | $T_{max}$ |
| --- | --- | --- | --- | --- |
| Form-13A | 4246.02 | 4454.15 | 223.89 | 3.85 |
| Absorica-40 mg | 3823.38 | 4045.01 | 229.02 | 2.71 |
| Ratio % | 111.05 | 110.11 | 97.75 | NA |

TABLE 7

Human Pharmacokinetic data for Form-13B and Absorica-40 mg

| Product | AUC0-t | AUC0-inf | Cmax | Tmax |
| --- | --- | --- | --- | --- |
| Form-13B | 5014.24 | 5484.76 | 273.35 | 3.74 |
| Absorica-40 mg | 4161.50 | 4479.39 | 246.92 | 3.43 |
| Ratio % | 120.49 | 122.44 | 110.70 | NA |

Figure 5:
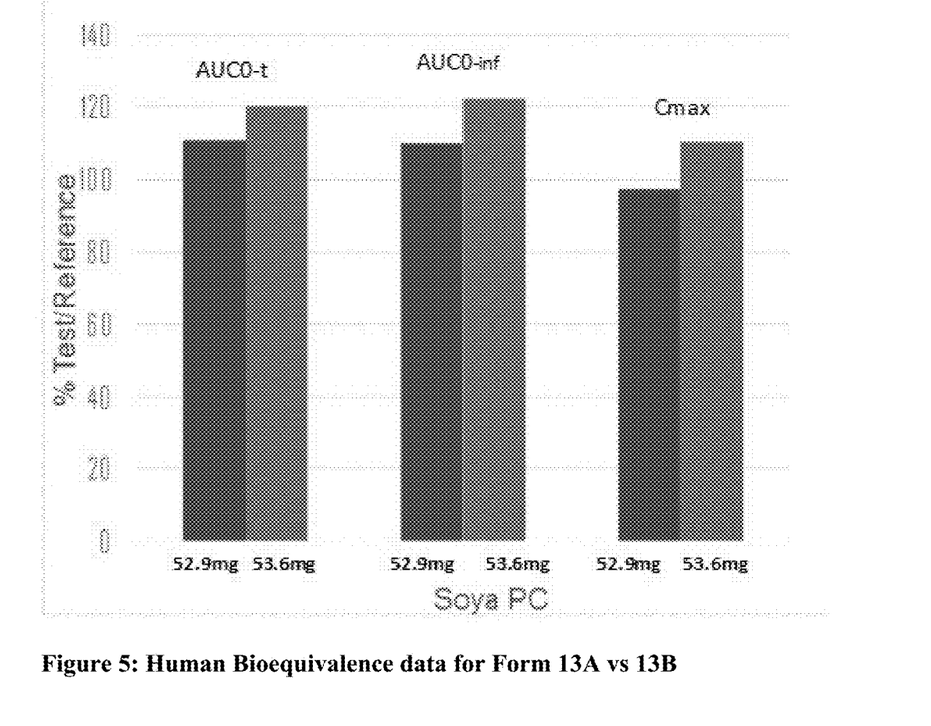
FIG. 5 is a graph showing human pharmacokinetic data from Example-4.

The rat data indicated that at Lipid: Drug ratio of 1.32, the values of Cmax and AUC for Test (Arithmetic means) were comparable to those of Absoric-40 mg (80-125%). It was also established that increase in Soya PC concentration increases AUC and Cmax further. Human data suggest that observations from rats directly co-relates to those of human. A moderate increase in Soya PC by 0.6 mg lead to close to a 105 point increase in AUC's and close to a 15% increase in Cmax (Form-13A vs B, in Tables 8-9 and FIG. 5); hence these findings corroborate the rat data.

Example 5: Isotretinoin Formulations and their Stability

The following formulations were prepared following the procedures of the above examples.

TABLE 8

Isotretinoin formulations with soya PC, cosolvent, etc.
Mg/Capsule

| Ingredients | Form-14 | Form-15 |
| --- | --- | --- |
| Isotretinoin | 40.00 | 40.00 |
| Soya PC | 52.90 | 52.90 |
| Propylene glycol | 67.74 | 67.74 |
| PEG 8000 | 100.65 | 100.65 |
| MCC | 273.55 | 174.19 |
| Aerosil | 7.74 | 15.48 |
| BHA | 0.97 | 0.97 |
| EDTA | 4.84 | 4.84 |
| BHT | 0.40 | 0.40 |
| Total | 548.79 | 457.17 |

A test of the stability of the formulations was then undertaken at 60° C. in an oven for 5 days. The results are provided below.

TABLE 9

Stability data of Form 14 and 15

| Formulation | Isotretinoin peak purity | Total impurities |
| --- | --- | --- |
| Form 14 @ 60° C./5 days | 98.90% | <1.20% |
| Form 15 @ 60° C./5 days | 99.08% | <1.00% |

This data shows that under accelerated conditions, the stability of the isotretinoin as evidenced by the peak purity and level of total impurities are greatly improved when compared to prior art formulations.

Example 6

In this example, comparative formulations were made without a cosolvent to demonstrate the advantages of including a cosolvent in the compositions of the invention. Formulations 16A-16C were prepared by dissolving Soya PC, BHA, and BHT in methylene chloride and Isotretinoin was dispersed in the solution. The rest of the dry excipient mixture was added to the liquid dispersion containing soya PC, Isotretinoin, BHA, BHT. The solvent was removed by vacuum in a desiccator.

TABLE 10

Isotretinoin formulations without cosolvent
Mg/Capsule

| Ingredients | 16A | 16B | 16C |
| --- | --- | --- | --- |
| Isotretinoin | 40.00 | 40.00 | 40.00 |
| Soya PC | 52.90 | 52.90 | 52.90 |
| BHA | 1.00 | 1.00 | 1.00 |
| BHT | 0.40 | 0.40 | 0.40 |
| Microcrystalline Cellulose (SMCC) (Premix of MCC and Silicon dioxide) | 275.00 | 0 | 0 |
| Lactose Anhydrous | 0 | 275.00 | 0 |
| Dicalcium Phosphate | 0 | 0 | 275.00 |
| EDTA Sodium | 0.25 | 0.25 | 0.25 |
| Sodium Bicarbonate | 0 | 5.00 | 0 |
| Total | 369.55 | 374.55 | 369.55 |
| Stability, 60° C./1 week | | | |
| Total Impurity (%) | 3.0% | 4.0% | 4.5% |

There is an unusual trend in the stability of the formulations. Usually the solid dosage forms which are devoid of water or any of the water miscible solvents tend to be more stable than liquid formulations. However, in the case of the formulations of this invention, the trend is different (opposite). The formulation with the water miscible solvent being absorbed onto solid excipients was found to be more stable than a similar formulation devoid of such solvent. This was completely unexpected and demonstrates that the presence of a liquid cosolvent during the formation of the powder compositions allows the protective effect of the antioxidants to coat or be in intimate contact with the drug particles adsorbed onto the particles of the cellulosic polymer, which is not the case with solid formulations made without a solvent.

Example 7

In this example, an alternative formulation was prepared to include alternative antioxidants. The formulation was made in the same way as set forth in the above examples.

TABLE 11

Isotretinoin formulations with different set of antioxidants

| | Form 17 | |
|---|---|---|
| Ingredients | Qty/Capsule (mg) | % W/W |
| Isotretinoin | 40.00 | 9.30 |
| Soya PC (Phospholipon 90G) | 52.90 | 12.30 |
| Propylene Glycol | 52.90 | 12.30 |
| PEG 8000 | 20.00 | 4.65 |
| MCC, Ceolus KG 1000 | 176.20 | 40.98 |
| Aerosil 200 | 80.00 | 18.60 |
| L-Ascorbic acid 6-palmitate | 6.00 | 1.40 |
| Propyl gallate | 2.00 | 0.47 |
| | 430.00 | 100.00 |

The formulation was then subjected to stability testing at 40° C./75% RH for various time points.

TABLE 12

Accelerated stability testing data of Form 17 (Packed in aluminum pouches)

| Parameter | 40° C./75% RH (1 month, 15 days) | 40° C./75% RH (2 month, 7 days) | 40° C./75% RH (3 months) |
|---|---|---|---|
| Assay | 105.00% | 104.00% | 99.00% |
| Peak purity Impurity | 99.60% | 99.10% | 98.90% |
| Total impurity | 0.40% | 0.90% | 1.10% |
| Highest individual impurity | 0.30% | 0.38% | 0.50% |

Based on the data from Form 17, the isotretinoin is stable in composition containing propyl gallate and ascorbyl palmitate as stabilizing antioxidants.

Example 8

In this example, comparative formulations were prepared using a different phospholipid.

TABLE 13

Isotretinoin compositions with DSPC (Mg/capsule)

| Ingredients | 18A | 18B | 18C |
|---|---|---|---|
| Isotretinoin | 40.00 | 40.00 | 40.0 |
| Distearoyl glycero phosphatidyl choline (DSPC) | 52.90 | 52.90 | 52.90 |
| BHA | 1.00 | 1.00 | 1.00 |
| BHT | 0.40 | 0.40 | 0.40 |
| Microcrystalline cellulose | 275.00 | 0 | 0 |
| Lactose Anhydrous | 0 | 0 | 275.00 |
| Dicalcium Phosphate anhydrous | 0 | 275.00 | 0 |
| Sodium bicarbonate | 0 | 0 | 5.50 |
| Total | 369.30 | 369.30 | 374.80 |

TABLE 14

Stability data of Form 18A-C

| | 60° C./1 week | | |
|---|---|---|---|
| Parameter | 18A | 18B | 18C |
| Total impurities | 4.50% | 3.50% | 4.50% |

Formulations 18A-18C were prepared by dissolving Soya PC, BHA, and BHT in methylene chloride and Isotretinoin was dispersed in the solution. The rest of the excipient mixture was added to the liquid dispersion containing DSPC, Isotretinoin, BHA, BHT. The solvent was removed by vacuum in a desiccator. This is one example with a different lipid but no solvent. The stability was so poor without the solvent that it can be seen that the cosolvent is a key part of the formulations.

Example 9 Effect of Particle Size on the Dissolution of Isotretinoin

During the development of Isotretinoin capsule formulations with improved dissolution, a sudden drop in dissolution for one batch was observed compared to an essentially similar previous batch. After evaluating the various process parameters that could affect dissolution, it was finally found that the particle size of Isotretinoin had an impact on dissolution. The observed drop in dissolution for one of the batches was due to a difference in particle size. Hence the API was milled to get a different size distribution and the effect of dissolution was evaluated keeping composition the same. A formulation was therefore prepared using different sized isotretinoin particles.

TABLE 15

Formula composition for particle size (Mg/capsule)

| Ingredients | Qty/Capsule |
|---|---|
| Isotretinoin | 40.0 |
| Soya PC | 52.90 |
| Propylene glycol | 67.74 |
| PEG 8000 | 96.99 |
| Microcrystalline cellulose (MCC, Ceolus KG 1000) | 174.19 |

TABLE 15-continued

Formula composition for particle size (Mg/capsule)

| Ingredients | Qty/Capsule |
|---|---|
| Aerosil 200 | 59.35 |
| L Ascorbic acid 6-palmitate | 2.00 |
| Edetic acid (EDTA) | 4.83 |
| Propyl gallate | 2.00 |
| Total | 500.00 |

TABLE 16

Data for particle size effect on dissolution

| Formulation | Particle size | | % Dissolved |
|---|---|---|---|
| | D50 (μm) | D90 (μm) | (After 4 h) |
| Form 20 A (Unmilled API) | 121.62 | 264 | 65 |
| Form 20 B | 43.8 | 175.5 | 74.12 |
| Form 20-C | 25.05 | 96.22 | 88.13 |
| Form 20-D | 21.53 | 102.78 | 89.75 |

Dissolution media: 900 mL pH 7.5 buffer with 2.5% SLS and 1 g/L Pancreatin, RPM-150. It was revealed from the above study that desired levels of dissolution were obtained when the particle size of the isotretinoin was D90<150 μm.

OVERALL RESULTS

The examples above show that when there are increases in soya PC in the formulation, there is an accompanying increase in dissolution and also enhanced absorption in rats after oral dosing. The benefit of including soya PC is not linear, however, and diminishes when present in amounts in excess of 160% of the isotretinoin. Interestingly, it was also observed that the stability of the isotretinoin in a powder formulation is better when the compositions includes both soya PC and a cosolvent.

What is claimed is:

1. An oral formulation, comprising
isotretinoin,
a lipid excipient and
a cosolvent,
wherein the only lipid excipient present is soya phosphatidylcholine, and
wherein the ratio of isotretinoin to the lipid excipient is from about 1:1.2 to about 1:1.6.

2. The oral formulation of claim 1, wherein the ratio of isotretinoin to the lipid excipient is from about 1:1.3 to about 1:1.5.

3. The oral formulation of claim 1, further comprising a cellulosic polymer, silicon dioxide and, optionally an antioxidant,
wherein the cellulosic polymer and the silicon dioxide are present as a mixture of particles and the isotretinoin, the lipid excipient, the cosolvent, and the optional antioxidant, are adsorbed on the particles of the mixture.

4. The oral formulation of claim 3, where in the cellulosic polymer is microcrystalline cellulose.

5. The oral formulation of claim 4, wherein the particle mixture includes microcrystalline cellulose and silicon dioxide.

6. The oral formulation of claim 1, wherein the cosolvent is selected from the group consisting of aliphatic alcohols, polyethylene glycols, propylene glycol, dimethyl formamide, dimethyl acetamide, glycerin and mixtures thereof.

7. The oral formulation of claim 6, wherein the cosolvent is propylene glycol.

8. The oral formulation of claim 6, wherein cellulosic polymer is microcrystalline cellulose, and the cosolvent is propylene glycol.

9. The oral formulation of claim 8, further comprising an auxiliary cosolvent.

10. The oral formulation of claim 9, wherein the auxiliary cosolvent is PEG, having a molecular weight of from about 1,000 to about 100,000.

11. The oral formulation of claim 1, wherein the amount of isotretinoin is from about 2 to about 20% wt. or from about 5 to about 15% wt.

12. The oral formulation of claim 1, wherein the amount of the lipid excipient is from about 5 to about 30% wt. or from about 5 to about 15% wt.

13. The oral formulation of claim 1, wherein the amount of cosolvent is from about 5 to about 30% wt. or from about 6 to about 15% wt.

14. The oral formulation of claim 3, wherein the amount of the cellulosic polymer is from about 10 to about 60% wt. or from about 5 to about 50% wt.

15. The oral formulation of claim 3, wherein the antioxidant is selected from the group consisting of BHA, EDTA, BHT, Propyl gallate, ascorbyl palmitate and mixtures thereof.

16. The oral formulation of claim 1 wherein the oral formulation is in the form of a softgel.

17. The oral formulation of claim 1 wherein the oral formulation is in the form of a dry powder.

* * * * *